(12) United States Patent
Dalko

(10) Patent No.: US 10,117,816 B2
(45) Date of Patent: *Nov. 6, 2018

(54) COSMETIC PROCESS FOR TREATING HUMAN BODY ODOR USING A 4-(3-ETHOXY-4-HYDROXYPHENYL)ALKYL KETONE OR 2-ETHOXY-4-HYDROXYALKYLPHENOL COMPOUND

(75) Inventor: Maria Dalko, Versailles (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/007,853

(22) PCT Filed: Mar. 29, 2012

(86) PCT No.: PCT/FR2012/050669
§ 371 (c)(1),
(2), (4) Date: Nov. 5, 2013

(87) PCT Pub. No.: WO2012/131266
PCT Pub. Date: Oct. 4, 2012

(65) Prior Publication Data
US 2014/0050684 A1 Feb. 20, 2014

Related U.S. Application Data

(60) Provisional application No. 61/471,441, filed on Apr. 4, 2011.

(30) Foreign Application Priority Data

Apr. 1, 2011 (FR) ...................................... 11 52795

(51) Int. Cl.
A61K 8/35 (2006.01)
A61K 8/34 (2006.01)
A61K 8/02 (2006.01)
A61Q 15/00 (2006.01)

(52) U.S. Cl.
CPC .............. *A61K 8/35* (2013.01); *A61K 8/0229* (2013.01); *A61K 8/347* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 6,488,919 B1 | 12/2002 | Murphy et al. | |
| 2004/0091628 A1* | 5/2004 | Heltovics | A61K 8/738 427/402 |
| 2010/0196484 A1* | 8/2010 | Aubrun | A61K 8/19 424/489 |
| 2012/0263768 A1* | 10/2012 | Marion | A61K 8/35 424/401 |

FOREIGN PATENT DOCUMENTS

| | | | |
|---|---|---|---|
| CN | 1462792 A | 12/2003 | |
| CN | 1462797 A | 12/2003 | |
| CN | 101829346 A * | 9/2010 | |
| FR | 2950883 A1 * | 4/2011 | ............. A61K 8/347 |
| FR | 2962328 A1 * | 1/2012 | ............... A61K 8/35 |
| JP | 2002-255774 A | 9/2002 | |
| WO | WO-98/30201 A1 | 7/1998 | |
| WO | WO-2011039445 A1 | 4/2011 | |

OTHER PUBLICATIONS

Zingerone structure confirmed by Scifinder (https://scifinder.cas.org/scifinder/view/scifinder/scifinderExplore.jsf, last visit Dec. 18, 2015).*
FR2962328A1 machine translation (Dec. 18, 2015).*
CN 101829346A Google English Translation ([retrieved from online website http://www.google.com/patents/CN101829346A, Feb. 25, 2017]).*
Berline "Derivatives of Zingerone.III", The Journal of General Chemistry of the U.S.S.R. vol. 19, 1949, pp. 1-11 (Year: 1949).*
Encyclopedia of magical and natural treatment without side effects, p. 224, 2004.

* cited by examiner

*Primary Examiner* — Ernst V Arnold
*Assistant Examiner* — Kyung S Chang
(74) *Attorney, Agent, or Firm* — Polsinelli PC

(57) ABSTRACT

The present invention relates to a cosmetic process for treating human body odor, in particular underarm odor, which consists in applying to human keratin materials a composition containing, in a cosmetically acceptable medium, at least one 4-(3-ethoxy-4-hydroxyphenyl)alkyl ketone or 2-ethoxy-4-hydroxyalkylphenol compound of formula (I) below:

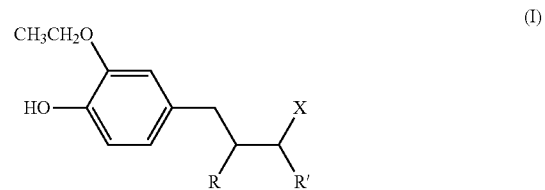

in which:
R represents a hydrogen atom, or a linear or branched, saturated or unsaturated (alkyl or alkenyl), $C_1$-$C_{18}$ hydrocarbon-based radical;
R' represents a linear or branched, saturated or unsaturated (alkyl or alkenyl), $C_1$-$C_{18}$ hydrocarbon-based radical, optionally substituted with a hydroxyl group;
C—X represents C=O or CH—OH.

The invention also relates to the cosmetic use of at least one compound of formula (I), as a deodorant active agent.

19 Claims, No Drawings

COSMETIC PROCESS FOR TREATING HUMAN BODY ODOR USING A 4-(3-ETHOXY-4-HYDROXYPHENYL)ALKYL KETONE OR 2-ETHOXY-4-HYDROXYALKYLPHENOL COMPOUND

CROSS REFERENCE TO RELATED APPLICATIONS

This application is a National Phase filing under 35 U.S.C. § 371 of PCT/FR2012/050669 filed on Mar. 29, 2012; and this application claims priority to Application No. 1152795 filed in France on Apr. 1, 2011; which claims the benefit of U.S. Provisional Application No. 61/471,441 filed on Apr. 7, 2011; the entire contents of all are hereby incorporated by reference.

The present invention relates to a cosmetic process for treating human body odor, in particular underarm odor, which consists in applying to human keratin materials a composition containing, in a cosmetically acceptable medium, at least one 4-(3-ethoxy-4-hydroxyphenyl)alkyl ketone or 2-ethoxy-4-hydroxyalkylphenol compound of formula (I).

The invention also relates to the cosmetic use of at least one 4-(3-ethoxy-4-hydroxyphenyl)alkyl ketone or 2-ethoxy-4-hydroxyalkylphenol compound of formula (I), as a deodorant active agent.

In the cosmetic field, it is well known to use, in topical application, deodorant products containing active substances of bactericidal type for reducing or even preventing the generally unpleasant underarm odor.

Eccrine or apocrine sweat has little odor when it is secreted. It is its degradation by bacteria via enzymatic reactions that produces malodorous compounds. Deodorant active agents have the function of reducing or preventing the formation of unpleasant odors. The various systems proposed hitherto may be grouped into major families. Among them are bactericidal substances that destroy the resident bacterial flora. The product most commonly used is Triclosan. There are also substances that reduce bacterial growth. Among these substances, mention may be made of transition-metal chelating agents such as ethylenediaminetetraacetic acid (EDTA) or diethylenetriaminepentaacetic acid (DPTA).

However, these various treatments applied to the skin of the armpits have a tendency to cause skin impairments reflected by irregularities and inhomogeneities such as pigmentary marks in particular on Asiatic skin, dyschromia or blackheads often caused by regrowth of the hair.

The need thus remains to find novel deodorant active agents which are effective and which do not have the drawbacks mentioned previously.

The Applicant has discovered, surprisingly and unexpectedly, that by using a composition of at least one 4-(3-ethoxy-4-hydroxyphenyl)alkyl ketone or 2-ethoxy-4-hydroxyalkylphenol compound of formula (I), the definition of which will be given later, it is possible to obtain efficient deodorant activity without the drawbacks mentioned previously.

This discovery forms the basis of the invention.

One subject of the present invention is thus a cosmetic process for treating human body odor, in particular underarm odor, which consists in applying to human keratin materials a composition containing, in a cosmetically acceptable medium, at least one 4-(3-ethoxy-4-hydroxyphenyl)alkyl ketone or 2-ethoxy-4-hydroxyalkylphenol compound of formula (I) which will be defined in detail so hereinbelow.

The invention also relates to the cosmetic use of at least one 4-(3-ethoxy-4-hydroxyphenyl)alkyl ketone or 2-ethoxy-4-hydroxyalkylphenol compound of formula (I), which will be defined in detail hereinbelow, as a deodorant active agent.

The invention also relates to a composition conditioned
(i) in pressurized form in an aerosol device or in a pump-dispenser bottle;
(ii) in a device equipped with a perforated wall, especially a grate;
(iii) in a device equipped with a ball applicator ("roll-on");
(iv) in the form of a wand (stick);
(v) in the form of a loose or compacted powder, characterized in that it contains, in a cosmetically acceptable medium, at least one compound of formula (I). Said composition may also comprise at least one antiperspirant active agent and/or at least one additional deodorant active agent.

The invention equally relates to a composition also comprising at least one antiperspirant active agent and/or at least one additional deodorant active agent.

According to a particular form, the compositions of the invention will not comprise any essential oil.

According to another particular form, the compositions of the invention will be different from a composition comprising at least one essential oil and from 0.5% to 5% of at least one 4-(3-ethoxy-4-hydroxyphenyl)alkyl ketone compound of formula (I).

The term "composition not comprising any essential oil" means comprising less than 0.01% by weight of essential oil relative to the total weight of the composition, or even being free of essential oil.

Other subjects of the invention will emerge later in the description.

The term "cosmetically acceptable medium" means a medium that is compatible with the skin and/or its integuments or mucous membranes, which has a pleasant color, odor and feel and which does not cause any unacceptable discomfort (stinging, tautness or redness) liable to discourage the consumer from using this composition.

The expression "human keratin materials" means the skin (body, face, area around the eyes), hair, eyelashes, eyebrows, body hair, nails, lips or mucous membranes.

According to the definition given in international standard ISO 9235 and adopted by the Commission of the European Pharmacopoeia, an essential oil is an odoriferous product generally of complex composition, obtained from a botanically defined plant raw material, either by steam entrainment, or by dry distillation, or via an appropriate mechanical process without heating (cold pressing). The essential oil is generally separated from the aqueous phase via a physical process which so does not result in any significant change in the composition.

The 4-(3-ethoxy-4-hydroxyphenyl)alkyl ketone or 2-ethoxy-4-hydroxyalkylphenol compounds of formula (I) in accordance with the invention correspond to the general formula (I) below:

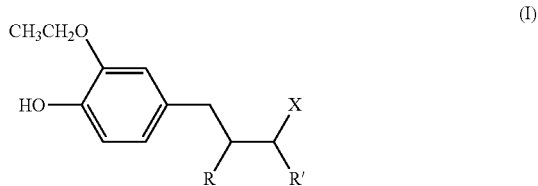

in which:
R represents a hydrogen atom, or a linear or branched, saturated or unsaturated (alkyl or alkenyl), $C_1$-$C_6$ hydrocarbon-based radical;
R' represents a linear or branched, saturated or unsaturated (alkyl or alkenyl), $C_1$-$C_{18}$ hydrocarbon-based radical, optionally substituted with a hydroxyl group;
C—X represents C=O or CH—OH.

Preferably, R represents H, methyl or ethyl.
Preferably, R' represents a saturated $C_1$-$C_6$, or unsaturated $C_2$-$C_6$, linear hydrocarbon-based radical, optionally substituted with a hydroxyl group.
Preferably, the compounds correspond to formula (I), in which:
when —C—X represents C=O, R denotes hydrogen and R' represents a linear $C_1$-$C_6$ alkyl radical, optionally substituted with an OH, and more preferentially R' denotes methyl or ethyl; or
when —C—X represents CH—OH, R denotes hydrogen and R' represents a linear $C_1$-$C_6$ alkyl radical, optionally substituted with an OH, and more preferentially R' denotes methyl or ethyl.

A mixture of compounds of formula (I) may, of course, be used.

Mention may preferably be made of compounds (1), (2) and (3) below:

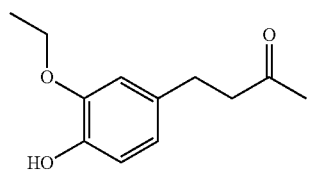

(1)

4-(3-ethoxy-4-hydroxyphenyl)-2-butanone(ethyl gingerone)

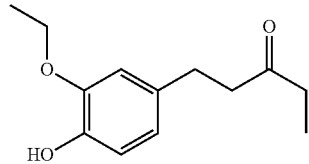

(2)

4-(3-ethoxy-4-hydroxyphenyl)-3-pentanone

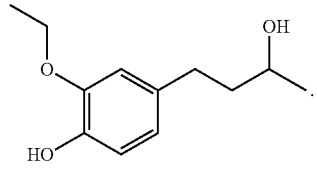

(3)

2-ethoxy-4-(3-hydroxybutyl)phenol

According to a particularly preferred form, compound (1) will be used.

The compounds of formula (I) may be readily prepared by a person skilled in the art on the basis of his general knowledge. Mention may be made in particular of the following bibliographic references: J. Asian Natural Products Research, 2006, 8(8), 683-688; Helv. Chimica Acta, 2006, 89(3), 483-495; Chem. Pharm. Bull., 2006, 54(3), 377-379; and Bioorg. Med. Chem. Lett., 2004, 14(5), 1287-1289.

They may thus be prepared from ethylvanillin, in the following manner:

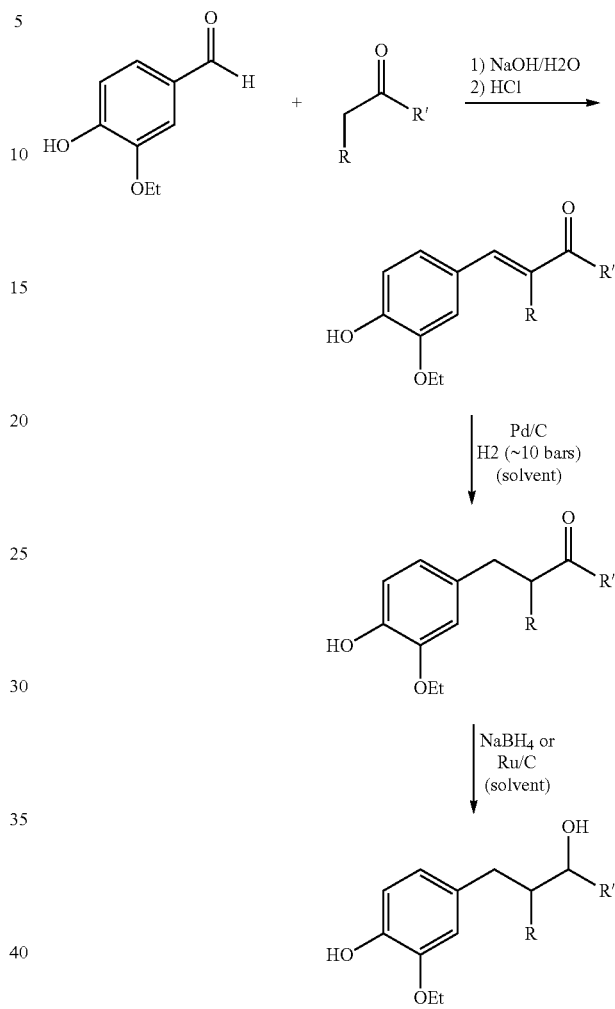

The compounds of formula (I) with C—X representing CHOH may be obtained by reduction of the corresponding compounds in which C—X represents C=O, for example by reduction with Ru/C or $NaBH_4$.

The compound(s) of formula (I) in accordance with the invention are present in the composition in concentrations preferably ranging from 0.01% to 10% by weight, even more preferentially from 0.5% to 5% by weight and even more particularly from 1% to 3% by weight, relative to the total weight of the composition.

Formulation Forms

The composition according to the invention can be provided in any formulation form conventionally used for a topical application and in particular in the form of aqueous gels or of aqueous or aqueous/alcoholic solutions. They may also, by addition of a fatty or oily phase, be provided in the form of dispersions of the lotion type, of emulsions with a liquid or semiliquid consistency of the milk type, obtained by dispersion of a fatty phase in an aqueous phase (O/W) or vice versa (W/O), or of suspensions or emulsions with a soft, semisolid or solid consistency of the cream or gel type, or alternatively of multiple emulsions (W/O/W or O/W/O), of microemulsions, of vesicular dispersions of ionic and/or nonionic type, or of wax/aqueous phase dispersions. These compositions are prepared according to the usual methods.

The compositions may especially be packaged in pressurized form in an aerosol device or in a pump dispenser; packaged in a device equipped with a perforated wall, especially a grate; packaged in a device equipped with a ball applicator ("roll-on"); packaged in the form of wands (sticks) or in the form of loose or compacted powder. In this regard, they contain the ingredients generally used in products of this type, which are well known to those skilled in the art.

According to another particular form of the invention, the compositions according to the invention may be anhydrous.

The term "anhydrous composition" means a composition containing less than 2% by weight of water, indeed even less than 0.5% of water, and especially devoid of water, the water not being added during the preparation of the composition but corresponding to the residual water contributed by the mixed ingredients.

According to another particular form of the invention, the compositions according to the invention may be solid, in particular in wand or stick form.

The term "solid composition" means that the measurement of the maximum force measured by texturometry during the penetration of a probe into the sample of formula must be at least equal to 0.25 newtons, in particular at least equal to 0.30 newtons and especially at least equal to 0.35 newtons, assessed under precise measurement conditions as follows.

The formulae are poured hot into jars 4 cm in diameter and 3 cm deep. Cooling is performed at room temperature. The hardness of the formulae produced is measured after an interval of 24 hours. The jars containing the samples are characterized in texturometry using a texture analyzer such as the machine sold by the company Rheo TA-XT2, according to the following protocol: a stainless-steel ball probe 5 mm in diameter is brought into contact with the sample at a speed of 1 mm/s. The measurement system detects the interface with the sample, with a detection threshold equal to 0.005 newtons. The probe penetrates 0.3 mm into the sample, at a speed of 0.1 mm/s. The measuring machine records the change in force measured in compression over time, during the penetration phase. The hardness of the sample corresponds to the average of the maximum force values detected during penetration, over at least three measurements.

Aqueous Phase

The compositions according to the invention intended for cosmetic use may comprise at least one aqueous phase. They are especially formulated as aqueous lotions or as water-in-oil or oil-in-water emulsions or as multiple emulsions (oil-in-water-in-oil or water-in-oil-in-water triple emulsions (such emulsions are known and described, for example, by C. Fox in "Cosmetics and Toiletries"-November 1986-Vol. 101-pages 101-112)).

The aqueous phase of said compositions contains water and generally other water-soluble or water-miscible solvents. The water-soluble or water-miscible solvents comprise short chain, for example $C_1$-$C_4$, monoalcohols, such as ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol and glycerol and propane-1,3-diol will be used more particularly.

Emulsifiers a) Oil-in-Water Emulsifiers

As emulsifiers that may be used in the oil-in-water emulsions or oil-in-water-in-oil triple emulsions, examples that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof, such as the mixture of glyceryl stearate and PEG-40 stearate.

Mention may also be made of fatty alcohol/alkylpolyglycoside emulsifying mixtures as described in patent applications WO 92/06778, WO 95/13863 and WO 98/47610, for instance the commercial products sold by the company SEPPIC under the name Montanov®.

b) Water-in-Oil Emulsifiers

Among the emulsifiers that may be used in the water-in-oil emulsions or water-in-oil-in-water-in-oil triple emulsions or triple emulsions, examples that may be mentioned include alkyl dimethicone copolyols corresponding to formula (I) below:

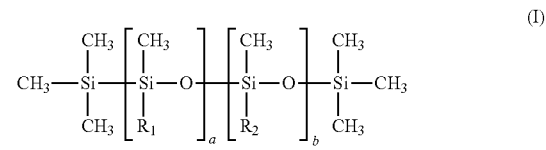

in which:

$R_1$ denotes a linear or branched $C_{12}$-$C_{20}$ and preferably $C_{12}$-$C_{18}$ alkyl group;

$R_2$ denotes the group: —$C_nH_{2n}$—(—$OC_2H_4$—)$_x$—(—$OC_3H_6$—)$_y$—O—$R_3$;

$R_3$ denotes a hydrogen atom or a linear or branched alkyl radical comprising from 1 to 12 carbon atoms;

a is an integer ranging from 1 to about 500;

b denotes an integer ranging from 1 to about 500;

n is an integer ranging from 2 to 12 and preferably from 2 to 5;

x denotes an integer ranging from 1 to about 50 and preferably from 1 to 30;

y denotes an integer ranging from 0 to about 49 and preferably from 0 to 29, with the proviso that, when y is other than zero, the ratio x/y is greater than 1 and preferably varies from 2 to 11.

Among the alkyl dimethicone copolyol emulsifiers of formula (I) that are preferred, mention will be made more particularly of Cetyl PEG/PPG-10/1 Dimethicone and more particularly the mixture Cetyl PEG/PPG-10/1 Dimethicone and Dimethicone (INCI name), for instance the product sold under the trade name Abil EM90 by the company Goldschmidt, or alternatively the mixture (Polyglyceryl-4 Stearate and Cetyl PEG/PPG-10 (and) Dimethicone (and) Hexyl Laurate), for instance the product sold under the trade name Abil WE09 by the same company.

Among the water-in-oil emulsifiers, mention may also be made of the dimethicone copolyols corresponding to formula (II) below:

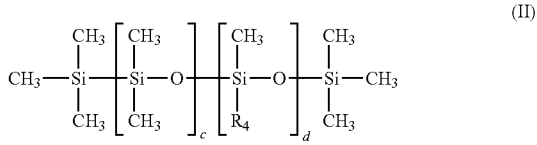 (II)

in which:

$R_4$ denotes the group: —$C_mH_{2m}$—(—$OC_2H_4$—)$_s$—(—$OC_3H_6$—)$_t$—O—$R_5$, $R_5$ denotes a hydrogen atom or a linear or branched alkyl radical comprising from 1 to 12 carbon atoms;

c is an integer ranging from 1 to about 500;

d denotes an integer ranging from 1 to about 500;

M is an integer ranging from 2 to 12 and preferably from 2 to 5;

s denotes an integer ranging from 1 to about 50 and preferably from 1 to 30;

t denotes an integer ranging from 0 to about 50 and preferably from 0 to 30; with the proviso that the sum s+t is greater than or equal to 1.

Among these preferential dimethicone copolyol emulsifiers of formula (II), use will particularly be made of PEG-18/PPG-18 Dimethicone and more particularly the mixture Cyclopentasiloxane (and) PEG-18/PPG-18 Dimethicone (INCI name), such as the product sold by the company Dow Corning under the trade name Silicone DC 5225 C or KF-6040 from the company Shin-Etsu.

According to a particularly preferred form, use will be made of a mixture of at least one emulsifier of formula (I) and of at least one emulsifier of formula (II).

Use will be made more particularly of a mixture of PEG-18/PPG-18 Dimethicone and Cetyl PEG/PPG-10/1 Dimethicone and even more particularly of a mixture of (Cyclopentasiloxane (and) PEG-18/PPG-18 Dimethicone) and of Cetyl PEG/PPG-10/1 Dimethicone and Dimethicone or of (Polyglyceryl-4 Stearate and Cetyl PEG/PPG-10 (and) Dimethicone (and) Hexyl Laurate).

Among the water-in-oil emulsifiers, mention may also be made of nonionic emulsifiers derived from fatty acids and polyols, alkylpolyglycosides (APGs), sugar esters and mixtures thereof.

As nonionic emulsifiers derived from fatty acids and polyols, use may be made especially of fatty acid esters of polyols, the fatty acid especially containing a $C_8$-$C_{24}$ alkyl chain, and the polyols being, for example, glycerol and sorbitan.

Fatty acid esters of polyols that may especially be mentioned include isostearic acid esters of polyols, stearic acid esters of polyols, and mixtures thereof, in particular isostearic acid esters of glycerol and/or sorbitan.

Stearic acid esters of polyols that may especially be mentioned include the polyethylene glycol esters, for instance PEG-30 Dipolyhydroxystearate, such as the product sold under the name Arlacel P135 by the company ICI.

Glycerol and/or sorbitan esters that may be mentioned, for example, include polyglyceryl isostearate, such as the product sold under the name Isolan GI 34 by the company Goldschmidt; sorbitan isostearate, such as the product sold under the name Arlacel 987 by the company ICI; sorbitan glyceryl isostearate, such as the product sold under the name Arlacel 986 by the company ICI, the mixture of sorbitan isostearate and polyglyceryl isostearate (3 mol) sold under the name Arlacel 1690 by the company Uniqema, and mixtures thereof.

The emulsifier may also be chosen from alkylpolyglycosides with an HLB of less than 7, for example those represented by the general formula (1) below:

$$R\text{—}O\text{-}(G)_x \quad (1)$$

in which R represents a branched and/or unsaturated alkyl radical comprising from 14 to 24 carbon atoms, G represents a reduced sugar comprising 5 or 6 carbon atoms, and x denotes a value ranging from 1 to 10 and preferably from 1 to 4, and G especially denotes glucose, fructose or galactose.

The unsaturated alkyl radical may comprise one or more ethylenically unsaturated groups, and in particular one or two ethylenically unsaturated groups.

As alkylpolyglycosides of this type, mention may be made of alkylpolyglucosides (G=glucose in formula (I)), and especially the compounds of formula (I) in which R more particularly represents an oleyl radical (unsaturated C18 radical) or an isostearyl radical (saturated C18 radical), G denotes glucose, x is a value ranging from 1 to 2, especially isostearyl glucoside or oleyl glucoside, and mixtures thereof. This alkylpolyglucoside may be used as a mixture with a coemulsifier, more especially with a fatty alcohol and especially a fatty alcohol containing the same fatty chain as that of the alkylpolyglucoside, i.e. comprising from 14 to 24 carbon atoms and containing a branched and/or unsaturated chain, and for example isostearyl alcohol when the alkylpolyglucoside is isostearyl glucoside, and oleyl alcohol when the alkylpolyglucoside is oleyl glucoside, optionally in the form of a self-emulsifying composition, as described, for example, in the document WO-A-92/06778. Use may be made, for example, of the mixture of isostearyl glucoside and isostearyl alcohol, sold under the name Montanov WO 18 by the company SEPPIC, and also the mixture of octyldodecanol and octyldodecyl xyloside sold under the name Fludanov 20X by the company SEPPIC.

Mention may also be made of succinic-terminated polyolefins, for instance esterified succinic-terminated polyisobutylenes and salts thereof, especially the diethanolamine salts, such as the products sold under the names Lubrizol 2724, Lubrizol 2722 and Lubrizol 5603 by the company Lubrizol or the commercial product Chemcinnate 2000.

The total amount of emulsifiers in the composition will preferably be, in the composition according to the invention, at active material contents ranging from 1% to 8% by weight and more particularly from 2% to 6% by weight, relative to the total weight of the composition.

Fatty Phase

The compositions according to the invention may contain at least one water-immiscible organic liquid phase, known as a fatty phase. This phase generally comprises one or more hydrophobic compounds that render said phase water-immiscible. Said phase is liquid (in the absence of structuring agent) at room temperature (20-25° C.). Preferentially, the water-immiscible organic liquid phase in accordance with the invention is generally constituted of at least one volatile oil and/or one non-volatile oil and optionally at least one structuring agent.

The term "oil" means a fatty substance that is liquid at room temperature (25° C.) and atmospheric pressure (760 mmHg, i.e. 105 Pa). The oil may be volatile or non-volatile.

For the purposes of the invention, the term "volatile oil" means an oil that is capable of evaporating on contact with the skin or the keratin fiber in less than one hour, at room temperature and atmospheric pressure. The volatile oils of the invention are volatile cosmetic oils, which are liquid at room temperature, having a nonzero vapor pressure, at room temperature and atmospheric pressure, ranging in particular from 0.13 Pa to 40000 Pa ($10^{-3}$ to 300 mmHg), in particular ranging from 1.3 Pa to 13000 Pa (0.01 to 100 mmHg) and more particularly ranging from 1.3 Pa to 1300 Pa (0.01 to 10 mmHg).

The term "nonvolatile oil" means an oil that remains on the skin or the keratin fiber at room temperature and atmospheric pressure for at least several hours, and that especially has a vapor pressure of less than $10^{-3}$ mmHg (0.13 Pa).

The oil may be chosen from any physiologically acceptable oil and in particular cosmetically acceptable oil, especially mineral, animal, plant or synthetic oils; in particular volatile or non-volatile hydrocarbon-based oils and/or silicone oils and/or fluoro oils, and mixtures thereof.

More precisely, the term "hydrocarbon-based oil" means an oil mainly comprising carbon and hydrogen atoms and optionally one or more functional groups chosen from hydroxyl, ester, ether and carboxylic functional groups. Generally, the oil has a viscosity of from 0.5 to 100000 mPa·s, preferably from 50 to 50000 mPa·s and more preferably from 100 to 300000 mPa·s.

As examples of volatile oils that may be used in the invention, mention may be made of:

volatile hydrocarbon-based oils chosen from hydrocarbon-based oils containing from 8 to 16 carbon atoms, and especially $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt by the company Shell, may also be used; volatile linear alkanes, such as those described in patent application DE10 2008 012 457 from the company Cognis.

volatile silicones, for instance volatile linear or cyclic silicone oils, especially those with a viscosity ≤8 centistokes ($8 \times 10^{-6}$ m²/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethyl-hexyltrisiloxane, heptamethyloctyltrisiloxane, hexamethyldisiloxane, octamethyl-trisiloxane, decamethyltetrasiloxane or dodecamethylpentasiloxane;
and mixtures thereof.

Mention may also be made of the volatile linear alkyltrisiloxane oils of general formula (I):

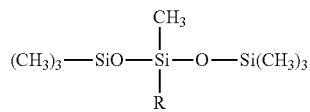

where R represents an alkyl group comprising from 2 to 4 carbon atoms, one or more hydrogen atoms of which can be replaced by a fluorine or chlorine atom.

Mention may be made, among the oils of general formula (I), of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

As examples of non-volatile oils that may be used in the invention, mention may be made of:
hydrocarbon-based oils of animal origin, such as perhydrosqualene;
hydrocarbon-based plant oils such as liquid triglycerides of fatty acids having 4 to 24 carbon atoms, for instance heptanoic or octanoic acid triglycerides, or else wheatgerm oil, olive oil, sweet almond oil, palm oil, rapeseed oil, cottonseed oil, alfalfa oil, poppyseed oil, pumpkin oil, marrow oil, blackcurrant oil, evening primrose oil, millet oil, barley oil, quinoa oil, rye oil, safflower oil, candlenut oil, passion flower oil, musk rose oil, sunflower oil, corn oil, soybean oil, grapeseed oil, sesame seed oil, hazelnut oil, apricot oil, macadamia oil, castor oil, avocado oil, caprylic/capric acid triglycerides, for instance those sold by the company Stéarineries Dubois or those sold under the names Miglyol 810, 812 and 818 by the company Dynamit Nobel, jojoba oil and shea butter oil;
linear or branched hydrocarbons, of mineral or synthetic origin, such as liquid paraffins and derivatives thereof, petroleum jelly, polydecenes, polybutenes, hydrogenated polyisobutene such as Parleam, or squalane;
synthetic ethers containing from 10 to 40 carbon atoms;
synthetic esters, especially of fatty acids, for instance the oils of formula $R_1COOR_2$ in which $R_1$ represents a linear or branched higher fatty acid residue containing from 1 to 40 carbon atoms and $R_2$ represents a hydrocarbon-based chain, which is especially branched, containing from 1 to 40 carbon atoms, with $R_1+R_2 \geq 10$, for instance Purcellin oil (cetostearyl octanoate), isononyl isononanoate, isopropyl myristate, isopropyl palmitate, $C_{12}$-$C_{15}$ alkyl benzoate, hexyl laurate, diisopropyl adipate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;
fatty alcohols that are liquid at room temperature, containing a branched and/or unsaturated carbon-based chain containing from 12 to 26 carbon atoms, for instance octyldodecanol, isostearyl alcohol, 2-butyloctanol, 2-hexyldecanol, 2-undecylpentadecanol or oleyl alcohol;
higher fatty acids such as oleic acid, linoleic acid or linolenic acid;
carbonates;
acetates;
citrates;
fluoro oils that are optionally partially hydrocarbon-based and/or silicone-based, for instance fluorosilicone oils, fluoro polyethers and fluorosilicones as described in the document EP-A-847 752;

silicone-based oils, for instance non-volatile linear or cyclic polydimethylsiloxanes (PDMSs); polydimethylsiloxanes comprising alkyl, alkoxy or phenyl groups, which are pendent or at the end of a silicone-based chain, these groups containing from 2 to 24 carbon atoms; phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates, and mixtures thereof.

Structuring Agent

The compositions according to the invention comprising a fatty phase may also contain at least one agent for structuring said fatty phase, which may preferably be chosen from waxes, pasty compounds, and mineral or organic lipophilic gelling agents, and mixtures thereof.

It is understood that the amount of these compounds may be adjusted by a person skilled in the art so as not to harm the effect desired in the context of the present invention.

Wax(es)

The wax is in general a lipophilic compound that is solid at room temperature (25° C.), with a reversible solid/liquid change in state, having a melting point of greater than or equal to 30° C., which may be up to 200° C. and in particular up to 120° C.

In particular, the waxes that are suitable for use in the invention may have a melting point of greater than or equal to 45° C. and in particular of greater than or equal to 55° C.

Within the meaning of the invention, the melting point corresponds to the temperature of the most endothermic peak observed in thermal analysis (DSC) as described in Standard ISO 11357-3; 1999. The melting point of the wax may be measured using a differential scanning calorimeter (DSC), for example the calorimeter sold under the name MDSC 2920 by the company TA Instruments.

The Measurement Protocol is as Follows:

A sample of 5 mg of wax placed in a crucible is subjected to a first temperature rise from −20° C. to 100° C., at a heating rate of 10° C./minute; it is then cooled from 100° C. to −20° C. at a cooling rate of 10° C./minute and it is finally subjected to a second temperature rise from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at room temperature of animal, plant, mineral or synthetic origin, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto wax, berry wax, shellac wax, Japan wax and sumac wax; montan wax, orange wax and lemon wax, refined sunflower wax sold under the name Sunflower Wax by Koster Keunen, microcrystalline waxes, paraffins and ozokerite; polyethylene waxes, the waxes obtained by the Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Mention may especially be made, among these waxes, of isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane)tetrastearate sold under the name Hest 2T-45® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax Castor 16L64® and 22L73® by the company Sophim, may also be used. Such waxes are described in patent application FR-A-2 792 190.

A wax that may be used is a $C_{20}$-$C_{40}$ alkyl(hydroxystearyloxy)stearate (the alkyl group containing from 20 to 40 carbon atoms), alone or as a mixture.

Such a wax is especially sold under the names "Kester Wax K 82 P®", "Hydroxypolyester K 82 P®" and "Kester Wax K 80 P®" by the company Koster Keunen.

As microwaxes that may be used in the compositions according to the invention, mention may be made especially of carnauba microwaxes, such as the product sold under the name MicroCare 350® by the company Micro Powders, synthetic microwaxes, such as the product sold under the name MicroEase 114S® by the company Micro Powders, microwaxes consisting of a mixture of carnauba wax and polyethylene wax, such as the products sold under the names Micro Care 300® and 310® by the company Micro Powders, microwaxes consisting of a mixture of carnauba wax and synthetic wax, such as the product sold under the name Micro Care 325® by the company Micro Powders, polyethylene microwaxes, such as the so products sold under the names Micropoly 200®, 220®, 220L® and 250S® by the company Micro Powders, the commercial products Performalene 400, Polyethylene and Performalene 500-L Polyethylene from New Phase Technologies, Performalene 655 Polyethylene or paraffin waxes, for instance the wax having the INCI name Microcrystalline Wax and Synthetic Wax and sold under the trade name Microlease by the company Sochibo; polytetrafluoroethylene microwaxes such as those sold under the names Microslip 519® and 519 L® by the company Micro Powders.

The composition according to the invention will preferably comprise a content of wax(es) ranging from 3% to 20% by weight relative to the total weight of the composition, in particular from 5% to 15% and more particularly from 6% to 15%.

According to a particular form of the invention, in the context of anhydrous solid compositions in stick form, use will be made of polyethylene microwaxes in the form of crystallites with an aspect ratio at least equal to 2, and with a melting point ranging from 70° C. to 110° C. and preferably from 70° C. to 100° C., in order to reduce or indeed even eliminate the presence of strata in the solid composition.

These crystallites in needle form and especially the dimensions thereof may be characterized visually according to the following method.

The wax is deposited on a microscope slide, which is placed on a hotplate. The slide and the wax are heated to a temperature generally at least 5° C. higher than the melting point of the wax or of the mixture of waxes under consideration. At the end of melting, the liquid thus obtained and the microscope slide are allowed to cool in order to solidify.

Observation of the crystallites is performed using a Leica DMLB100 optical microscope, with an objective lens selected as a function of the size of the objects to be viewed, and under polarized light. The dimensions of the crystallites are measured using image analysis software such as that sold by the company Microvision.

The crystallite polyethylene waxes in accordance with the invention preferably have an average length ranging from 5 to 10 µm. The term "average length" denotes the dimension given by the statistical particle size distribution at half the population, which is written as D50.

Use will be made more particularly of a mixture of Performalene 400 Polyethylene and Performalene 500-L Polyethylene waxes from New Phase Technologies.

Pasty Compounds

Within the meaning of the present invention, the term "pasty compound" is intended to denote a lipophilic fatty compound that undergoes a reversible solid/liquid change in state, which has in the solid form an anisotropic crystal organization, and which comprises, at a temperature of 23° C., a liquid fraction and a solid fraction.

The pasty compound is preferably chosen from synthetic compounds and compounds of plant origin. A pasty compound may be obtained by synthesis from starting materials of plant origin.

The pasty compound may be advantageously chosen from:
lanolin and derivatives thereof,
polymeric or non-polymeric silicone compounds,
polymeric or non-polymeric fluoro compounds,
vinyl polymers, especially:
olefin homopolymers,
olefin copolymers,
hydrogenated diene homopolymers and copolymers,
linear or branched oligomers, homopolymers or copolymers of alkyl(meth)acrylates preferably containing a $C_8$-$C_{30}$ alkyl group,
oligomers, homopolymers and copolymers of vinyl esters containing $C_8$-$C_{30}$ alkyl groups,
oligomers, homopolymers and copolymers of vinyl ethers containing $C_8$-$C_{30}$ alkyl groups,
liposoluble polyethers resulting from the polyetherification between one or more $C_2$-$C_{100}$ and preferably $C_2$-$C_{50}$ diols,
esters,
mixtures thereof.

Among the esters, the following are especially preferred:
esters of a glycerol oligomer, especially diglycerol esters, in particular condensates of adipic acid and of glycerol, for which some of the hydroxyl groups of the glycerols have reacted with a mixture of fatty acids such as stearic acid, capric acid, and isostearic acid and 12-hydroxystearic acid, especially such as those sold under the brand name Softisan 649 by the company Sasol,
the arachidyl propionate sold under the brand name Waxenol 801 by Alzo,
phytosterol esters,
fatty acid triglycerides and derivatives thereof,
pentaerythritol esters,
non-crosslinked polyesters resulting from polycondensation between a linear or branched $C_4$-$C_{50}$ dicarboxylic acid or polycarboxylic acid and a $C_2$-$C_{50}$ diol or polyol,
aliphatic esters of an ester, resulting from the esterification of an aliphatic hydroxycarboxylic acid ester with an aliphatic carboxylic acid,
polyesters resulting from the esterification, with a polycarboxylic acid, of an aliphatic hydroxycarboxylic acid ester, said ester comprising at least two hydroxyl groups, such as the products Risocast DA-H® and Risocast DA-L®,
esters of a diol dimer and of a diacid dimer, where appropriate esterified on their free alcohol or acid functional group(s) by acid or alcohol radicals, such as Plandool-G,
mixtures thereof.

Among the pasty compounds of plant origin that will preferably be chosen is a mixture of soybean sterols and of oxyethylenated (5 EO) oxypropylenated (5 PO) pentaerythritol, sold under the reference Lanolide by the company Vevy.

Lipophilic Gelling Agents

Mineral Gelling Agents

Mineral lipophilic gelling agents that may be mentioned include optionally modified clays, for instance hectorites modified with a C10-C22 ammonium chloride, for instance hectorite modified with distearyldimethylammonium chloride, for instance the product sold under the name Bentone 38V® by the company Elementis.

Mention may also be made of fumed silica optionally subjected to a hydrophobic surface treatment, the particle size of which is less than 1 µm. This is because it is possible to chemically modify the surface of the silica, by chemical reaction generating a reduced number of silanol groups present at the surface of the silica. It is possible especially to substitute silanol groups with hydrophobic groups; a hydrophobic silica is then obtained. The hydrophobic groups may be trimethylsiloxyl groups, which are obtained especially by treating fumed silica in the presence of hexamethyldisilazane. Silicas thus treated are known as "silica silylate" according to the CTFA (8th Edition, 2000). They are sold, for example, under the references Aerosil R812® by the company Degussa, CAB-O-SIL TS-530® by the company Cabot, or may be dimethylsilyloxyl or polydimethylsiloxane groups, which are obtained especially by treating fumed silica in the presence of polydimethylsiloxane or dimethyldichlorosilane. Silicas thus treated are known as "silica dimethyl silylate" according to the CTFA (8th Edition, 2000). They are sold, for example, under the references Aerosil R972® and Aerosil R974® by the company Degussa, and CAB-O-SIL TS-610® and CAB-O-SIL TS-720® by the company Cabot.

The hydrophobic fumed silica in particular has a particle size that may be nanometric to micrometric, for example ranging from about 5 to 200 nm.

Organic Gelling Agents

The polymeric organic lipophilic gelling agents are, for example, partially or totally crosslinked elastomeric organopolysiloxanes of three-dimensional structure, for instance those sold under the names KSG6®, KSG16® and KSG18® by Shin-Etsu, Trefil E-505C® or Trefil E-506C® from Dow Corning, Gransil SR-CYC®, SR DMF10®, SR-DC556®, SR 5CYC Gel®, SR DMF 10 Gel® and SR DC 556 Gel® from Grant Industries and SF 1204® and JK 113® from General Electric; ethylcellulose, for instance the product sold under the name Ethocel® by Dow Chemical; galactomannans comprising from one to six and in particular from two to four hydroxyl groups per saccharide, substituted with a saturated or unsaturated alkyl chain, for instance guar gum alkylated with C1 to C6, and in particular C1 to C3, alkyl chains, and mixtures thereof. Block copolymers of "diblock", "triblock" or "radial" type, of the polystyrene/polyisoprene or polystyrene/polybutadiene type, such as the products sold under the name Luvitol HSB® by the company BASF, of the polystyrene/copoly(ethylene-propylene)

type, such as the products sold under the name Kraton® by the company Shell Chemical Co., or of the polystyrene/copoly(ethylene-butylene) type, and mixtures of triblock and radial (star) copolymers in isododecane, such as those sold by the company Penreco under the name Versagel®, for instance the mixture of butylene/ethylene/styrene triblock copolymer and of ethylene/propylene/styrene star copolymer in isododecane (Versagel M 5960).

Lipophilic gelling agents that may also be mentioned include polymers with a weight-average molecular weight of less than 100000, comprising a) a polymer backbone with hydrocarbon-based repeating units containing at least one heteroatom, and optionally b) at least one optionally functionalized pendent fatty chain and/or at least one optionally functionalized terminal fatty chain, containing from 6 to 120 carbon atoms and being linked to these hydrocarbon-based units, as described in patent applications WO-A-02/056847 and WO-A-02/47619, in particular polyamide resins (especially comprising alkyl groups containing from 12 to 22 carbon atoms) such as those described in U.S. Pat. No. 5,783,657.

Among the lipophilic gelling agents that may be used in the compositions according to the invention, mention may also be made of fatty acid esters of dextrin, such as dextrin palmitates, especially the products sold under the names Rheopearl TL®, or Rheopearl KL® by the company Chiba Flour.

Silicone polyamides of the polyorganosiloxane type such as those described in documents U.S. Pat. No. 5,874,069, U.S. Pat. No. 5,919,441, U.S. Pat. No. 6,051,216 and U.S. Pat. No. 5,981,680 may also be used.

These silicone polymers may belong to the following two families:
  polyorganosiloxanes comprising at least two groups capable of establishing hydrogen interactions, these two groups being located in the chain of the polymer, and/or
  polyorganosiloxanes comprising at least two groups capable of establishing hydrogen interactions, these two groups being located on grafts or branches.

Additional Antiperspirant Agents

The composition of the invention as defined previously may also contain one or more additional antiperspirant agents, in particular aluminum and/or zirconium salts or complexes.

The antiperspirant salts or complexes in accordance with the invention are generally chosen from aluminum and/or zirconium salts or complexes. They are preferably chosen from aluminum halohydrates; aluminum zirconium halohydrates, complexes of zirconium hydroxychloride and of aluminum hydroxychloride with or without an amino acid, such as those described in U.S. Pat. No. 3,792,068.

Among the aluminum salts, mention may be made in particular of aluminum chlorohydrate in activated or unactivated form, aluminum chlorohydrex, the aluminum chlorohydrex-polyethylene glycol complex, the aluminum chlorohydrex-propylene glycol complex, aluminum dichlorohydrate, the aluminum dichlorohydrex-polyethylene glycol complex, the aluminum dichlorohydrex-propylene glycol complex, aluminum sesquichlorohydrate, the aluminum sesquichlorohydrex-polyethylene glycol complex, the aluminum sesquichlorohydrex-propylene glycol complex, and aluminum sulfate buffered with sodium aluminum lactate.

Among the aluminum-zirconium salts, mention may be made in particular of aluminum zirconium octachlorohydrate, aluminum zirconium pentachlorohydrate, aluminum zirconium tetrachlorohydrate and aluminum zirconium trichlorohydrate.

The complexes of zirconium hydroxychloride and of aluminum hydroxychloride with an amino acid are generally known as ZAG (when the amino acid is glycine). Among these products, mention may be made of the aluminum zirconium octachlorohydrex-glycine complexes, the aluminum zirconium pentachlorohydrex-glycine complexes, the aluminum zirconium tetrachlorohydrex-glycine complexes and the aluminum zirconium trichlorohydrex-glycine complexes.

The antiperspirant salts or complexes may be present in the composition according to the invention in a proportion from about 0.5% to 25% by weight relative to the total weight of the composition.

It is also possible to add moisture absorbers, for instance perlites and preferably expanded perlites.

The perlites that may be used according to the invention are generally aluminosilicates of volcanic origin and have the composition:
70.0-75.0% by weight of silica $SiO_2$
12.0-15.0% by weight of oxide of aluminum oxide $Al_2O_3$
3.0-5.0% of sodium oxide $Na_2O$
3.0-5.0% of potassium oxide $K_2O$
0.5-2% of iron oxide $Fe_2O_3 \rightarrow$
0.2-0.7% of magnesium oxide MgO
0.5-1.5% of calcium oxide CaO
0.05-0.15% of titanium oxide $TiO_2$ The perlite is ground, dried and then calibrated in a first step. The product obtained, known as perlite ore, is gray-colored and has a size of about 100 μm.

The perlite ore is subsequently expanded (1000° C./2 seconds) to give more or less white particles. When the temperature reaches 850-900° C., the water trapped in the structure of the material evaporates and brings about the expansion of the material, relative to its original volume. The expanded perlite particles in accordance with the invention may be obtained via the expansion process described in U.S. Pat. No. 5,002,698.

Preferably, the perlite particles used will be ground; in this case, they are known as Expanded Milled Perlite (EMP). They preferably have a particle size defined by a median diameter $D_{50}$ ranging from 0.5 to 50 μm and preferably from 0.5 to 40 μm.

Preferably, the perlite particles used have an untamped apparent density at 25° C. ranging from 10 to 400 $kg/m_3$ (standard DIN 53468) and preferably from 10 to 300 $kg/m^3$.

Preferably, the expanded perlite particles according to the invention have a water-absorbing capacity, measured at the wet point, ranging from 200% to 1500% and preferably from 250% to 800%.

The wet point corresponds to the amount of water which needs to be added to 1 g of particle in order to obtain a homogeneous paste. This method is derived directly from that of the oil uptake applied to solvents. The measurements are taken in the same way via the wet point and the flow point, which respectively have the following definitions:
wet point: weight, expressed in grams per 100 g of product, corresponding to the production of a homogeneous paste following the addition of a solvent to a powder.
flow point: weight expressed in grams per 100 g of product at and above which the amount of solvent is greater than the capacity of the powder to retain it. This is reflected by the production of a more or less homogeneous mixture that flows over the glass plate.

The wet point and the flow point are measured according to the following protocol:

Protocol for Measuring the Water Absorption

1) Equipment Used

Glass plate (25×25 mm)
Spatula (wooden shaft and metal part (15×2.7 mm))
Silk-bristled brush
Balance 2) Procedure The glass plate is placed on the balance and 1 g of perlite particles is weighed out. The beaker containing the solvent and the liquid sampling pipette are placed on the balance. The solvent is gradually added to the powder, the whole being regularly blended (every 3 to 4 drops) with the spatula.

The weight of solvent needed to obtain the wet point is noted. Further solvent is added and the weight which makes it possible to reach the flow point is noted. The mean of three tests will be determined.

The expanded perlite particles sold under the trade names Optimat 1430 OR or Optimat 2550 by the company World Minerals will be used in particular.

Deodorant Agents

The deodorant agents may be bacteriostatic agents or bactericides that act on underarm odor microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (Symclariol from the company Symrise), glycerol derivatives, for instance caprylic/capric glycerides (Capmul MCM from Abitec), glyceryl caprylate or caprate (Dermosoft GMCY and Dermosoft GMC, respectively from Straetmans), polyglyceryl-2 caprate (Dermosoft DGMC from Straetmans), and biguanide derivatives, for instance polyhexamethylene biguanide salts, chlorhexidine and salts thereof; 4-phenyl-4,4-dimethyl-2-butanol (Symdeo MPP from Symrise).

Among the deodorant active agents in accordance with the invention, mention may also be made of—zinc salts, for instance zinc salicylate, zinc gluconate, zinc pidolate; zinc sulfate, zinc chloride, zinc lactate, zinc phenolsulfonate; salicylic acid and derivatives thereof such as 5-(n-octanoyl) salicylic acid.

The deodorant active agents may be odor absorbers such as zinc ricinoleate, sodium bicarbonate; metallic or nonmetallic zeolites, cyclodextrins or alum.

They may also be a chelating agent such as Dissolvine GL-47-S from Akzo Nobel, EDTA; DPTA.

They may also be a polyol such as glycerol or propane-1,3-diol (Zemea Propanediol sold by Dupont Tate and Lyle Bioproducts).

Alternatively, they may be an enzyme inhibitor such as triethyl citrate.

In the event of incompatibility or to stabilize them, some of the agents mentioned above may be incorporated into spherules, especially ionic or nonionic vesicles, and/or particles (capsules and/or spheres).

The deodorant agents may preferably be present in the compositions according to the invention in weight concentrations ranging from 0.01% to 15% by weight relative to the total weight of the composition.

Organic Powder

According to one particular form of the invention, the compositions according to the invention will also contain an organic powder.

In the present application, the term "organic powder" means any solid that is insoluble in the medium at room temperature (25° C.).

As organic powders that may be used in the composition of the invention, examples that may be mentioned include polyamide particles and especially those sold under the Orgasol names by the company Atochem; nylon-6,6 fibers, especially the polyamide fibers sold by Etablissements P Bonte under the name Polyamide 0.9 Dtex 0.3 mm (INCI name: Nylon-6,6 or Polyamide 6,6) with a mean diameter of 6 μm, a weight of about 0.9 dtex and a length ranging from 0.3 mm to 1.5 mm; polyethylene powders; microspheres based on acrylic copolymers, such as those made of ethylene glycol dimethacrylate/lauryl methacrylate copolymer, sold by the company Dow Corning under the name Polytrap; polymethyl methacrylate microspheres, sold under the name Microsphere M-100 by the company Matsumoto or under the name Covabead LH85 by the company Wackherr; hollow polymethyl methacrylate microspheres (particle size: 6.5-10.5 μm) sold under the name Ganzpearl GMP 0800 by Ganz Chemical; methyl methacrylate/ethylene glycol dimethacrylate copolymer microbeads (size: 6.5-10.5 μm) sold under the name Ganzpearl GMP 0820 by Ganz Chemical or Microsponge 5640 by the company Amcol Health & Beauty Solutions; ethylene-acrylate copolymer powders, such as those sold under the name Flobeads by the company Sumitomo Seika Chemicals; expanded powders such as hollow microspheres and especially microspheres formed from a terpolymer of vinylidene chloride, acrylonitrile and methacrylate and sold under the name Expancel by the company Kemanord Plast under the references 551 DE 12 (particle size of about 12 μm and mass per unit volume of 40 kg/m$^3$), 551 DE 20 (particle size of about 30 μm and mass per unit volume of 65 kg/m$^3$), 551 DE 50 (particle size of about 40 μm), or the microspheres sold under the name Micropearl F 80 ED by the company Matsumoto; powders of natural organic materials such as starch powders, especially of crosslinked or non-crosslinked corn, wheat or rice starch, such as the powders of starch crosslinked with octenylsuccinic anhydride, sold under the name Dry-Flo by the company National Starch; silicone resin microbeads such as those sold under the name Tospearl by the company Toshiba Silicone, especially Tospearl 240; amino acid powders such as the lauroyllysine powder sold under the name Amihope LL-11 by the company Ajinomoto; particles of wax microdispersion, which preferably have mean sizes of less than 1 μm and especially ranging from 0.02 μm to 1 μm, and which are formed essentially from a wax or a mixture of waxes, such as the products sold under the name Aquacer by the company Byk Cera, and especially: Aquacer 520 (mixture of synthetic and natural waxes), Aquacer 514 or 513 (polyethylene wax), Aquacer 511 (polymeric wax), or such as the products sold under the name Jonwax 120 by the company Johnson Polymer (mixture of polyethylene wax and paraffin wax) and under the name Ceraflour 961 by the company Byk Cera (micronized modified polyethylene wax); and mixtures thereof.

Additives

The cosmetic compositions according to the invention may also comprise cosmetic adjuvants chosen from softeners, antioxidants, opacifiers, stabilizers, moisturizers, vitamins, bactericides, preserving agents, polymers, fragrances, thickeners or suspension agents, propellants or any other ingredient usually used in cosmetics for this type of application.

Needless to say, a person skilled in the art will take care to select this or these optional additional compounds such that the advantageous properties intrinsically associated with the cosmetic composition in accordance with the invention are not, or are not substantially, adversely affected by the envisioned addition(s).

According to one embodiment, a composition according to the invention will not comprise any essential oil.

Thickeners and Suspension Agents

The thickeners may be chosen from carboxyvinyl polymers, such as Carbopols so (Carbomers) and Pemulens (acrylate/$C_{10}$-$C_{30}$ alkyl acrylate copolymer); polyacrylamides, for instance the crosslinked copolymers sold under the names Sepigel 305 (CTFA name: polyacrylamide/$C_{13-14}$ isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Hoechst under the trade name Hostacerin AMPS (CTFA name: ammonium polyacryloyldimethyl taurate or Simulgel 800 sold by the company SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 sold by the company SEPPIC; cellulose derivatives such as hydroxyethylcellulose or cetylhydroxyethylcellulose; polysaccharides and especially gums such as xanthan gum and hydroxypropyl guar gums; silicas, for instance Bentone Gel MIO sold by the company NL Industries or Veegum Ultra sold by the company Polyplastic.

The thickeners may also be cationic, for instance Polyquaternium-37 sold under the name Salcare SC95 (Polyquaternium-37 (and) Mineral Oil (and) PPG-1 Trideceth-6) or Salcare SC96 (Polyquaternium-37 (and) Propylene Glycol Dicaprylate/Dicaprate (and) PPG-1 Trideceth-6) or other crosslinked cationic polymers, for instance those of the CTFA name Ethyl Acrylate/Dimethylaminoethyl Methacrylate Cationic Copolymer In Emulsion.

Suspension Agents

In order to improve the homogeneity of the product, it is also possible to use one or more suspension agents preferably chosen from hydrophobic modified montmorillonite clays such as hydrophobic modified bentonites or hectorites. Examples that may be mentioned include the product Stearalkonium Bentonite (CTFA name) (product of reaction of bentonite and the quaternary ammonium stearalkonium chloride) such as the commercial product sold under the name Tixogel MP 250 by the company Sud Chemie Rheologicals, United Catalysts Inc. or the product Disteardimonium Hectorite (CTFA name) (product of reaction of hectorite and distearyldimonium chloride) sold under the name Bentone 38 or Bentone Gel by the company Elementis Specialities.

Other suspension agents may be used, in the present case in hydrophilic (aqueous and/or ethanolic) media. They may be cellulose, xanthan, guar, starch, locust bean or agar agar derivatives.

The suspension agents are preferably present in amounts ranging from 0.1% to 5% by weight and more preferentially from 0.2% to 2% by weight relative to the total weight of the composition.

The amounts of these various constituents that may be present in the cosmetic composition according to the invention are those conventionally used in compositions for treating perspiration.

Aerosols

The compositions according to the invention may also be pressurized and may be packaged in an aerosol device formed by:

(A) a container comprising an antiperspirant composition as defined previously,
(B) at least one propellant and a means for dispensing said aerosol composition.

The propellants generally used in products of this type and that are well known to those skilled in the art are, for instance, dimethyl ether (DME); volatile hydrocarbons such as n-butane, propane, isobutane and mixtures thereof, optionally with at least one chlorinated and/or fluorinated hydrocarbon; among the latter, mention may be made of the compounds sold by the company DuPont de Nemours under the names Freon® and Dymel®, and in particular monofluorotrichloromethane, difluorodichloromethane, tetrafluorodichloroethane and 1,1-difluoroethane sold especially under the trade name Dymel 152 A by the company DuPont. Carbon dioxide, nitrous oxide, nitrogen or compressed air may also be used as propellant.

The compositions containing perlite particles as defined previously and the propellant(s) may be in the same compartment or in different compartments in the aerosol container. According to the invention, the concentration of propellant generally varies from 5% to 95% by weight of pressurized composition, and more preferentially from 50% to 85% by weight relative to the total weight of the pressurized composition.

The dispensing means, which forms a part of the aerosol device, is generally formed by a dispensing valve controlled by a dispensing head, which itself comprises a nozzle via which the aerosol composition is vaporized. The container containing the pressurized composition may be opaque or transparent. It may be made of glass, polymer or metal, optionally coated with a protective varnish coat.

EXAMPLE 1: SOAP STICK

| | |
|---|---|
| Ethyl gingerone | 2 g |
| Sodium stearate | 3.50 g |
| Behenic acid (rapeseed extract) | 0.75 g |
| Oxyethylenated stearyl alcohol (100 EO) | 3.00 g |
| Ethylenediaminetetraacetic acid (EDTA) | 0.50 g |
| Pure sodium hydroxide | qs pH = 7 |
| Glycerol | 20.00 g |
| Propylene glycol | 50.00 g |
| Deionized water | qs 100 |

The composition has a deodorant effect.

Demonstration of the Bactericidal Activity of a Composition Toward the Microorganisms Involved in Underarm Odor The test described herein allows a quantitative determination of the bactericidal activity of a composition on microorganisms under optimal growth conditions, namely microorganisms of the type *Corynebacterium xerosis* (Institut Pasteur Collection No. 5216) cultured on tryptocasein soy agar on a slant.

On the day before the test, 32 g of tryptocasein soy broth are placed in a pill bottle and incubated at 35° C. On the day of the test, 4 g of the test composition are added and the mixture is homogenized with a vortex blender.

A product-free growth control is prepared under the same conditions (4 g of tryptone salt diluent in place of the test composition) in order to check that the microorganisms are under favorable growth conditions throughout the test.

For the preparation of the inoculum, five days before the start of the test, the bacterial strain is subcultured on a suitable medium. It is incubated for 5 days at 35° C. On the day of the test, the slant is washed with about 9 ml of diluent: the suspension obtained has a titer of $10^8$ microorganisms/ml (counting is performed).

On the day of the test, 4 ml of inoculum are placed in the pill bottle containing the test composition and also in the control pill bottle, which corresponds to a rate of $10^7$ bacteria per gram of preparation. The pill bottles are placed in a stirred incubator (35° C.-200 rpm).

After 24 hours of contact, the contents of the pill bottles are homogenized using a vortex blender. Decimal dilutions are performed in neutralizing medium (Eugon LT 100 broth). Agar (Eugon LT 100 medium) is deposited on the surface of Petri dishes. The Petri dishes are incubated in an oven at 35° C. for 5 days. The colonies on the dishes containing more than 20 and less than 200 colonies are counted.

The difference between the decimal logarithm of the number of bacteria found after 24 hours of contact for the test composition and the decimal logarithm of the number of bacteria found after 24 hours of contact for the control is calculated.

EXAMPLE 2 BELOW, WHICH IS A DEODORANT AQUEOUS GEL, WAS PREPARED

| | |
|---|---|
| Acrylates/C10-C30 alkyl acrylate crosspolymer (Carbopol Ultrez 20 Polymer-Lubrizol) | 0.9 g |
| Pure sodium hydroxide | qs pH = 7 |
| Ethyl gingerone | 2 g |
| Polyethylene glycol (8 EO)or PEG-8 | 6 g |
| Citric acid | 0.33 g |
| Demineralized water | qs 100 g |

The deodorant activity results obtained on the composition of Example 2 are collated in the following table:

| Composition | Reduction after 24 hours of the population of microorganisms relative to the control |
|---|---|
| Strain | *Corynebacterium xerosis* |
| 2 (invention) | 1 log |

Composition 2 has a deodorant effect.

The invention claimed is:
1. A composition conditioned
   (i) in pressurized form in an aerosol device or in a pump-dispenser bottle;
   (ii) in a device equipped with a perforated wall;
   (iii) in a device equipped with a ball applicator;
   (iv) in the form of a wand;
   (v) in the form of a loose or compacted powder, the composition contains, in a cosmetically acceptable medium, at least one compound of formula (I)

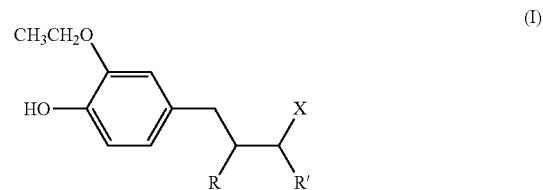

in which:
R represents a hydrogen atom, or a linear or branched, saturated or unsaturated (alkyl or alkenyl), $C_1$-$C_6$ hydrocarbon-based radical;
R' represents a linear or branched, saturated or unsaturated (alkyl or alkenyl), $C_1$-$C_{18}$ hydrocarbon-based radical, optionally substituted with a hydroxyl group;
C—X represents C═O or CH—OH wherein the composition comprises 1% to 5% by weight of at least one 4-(3-ethoxy-4-hydroxyphenyl)alkyl ketone compound of formula (I) relative to the total weight of the composition and wherein the composition does not comprise an essential oil.

2. The composition as claimed in claim 1, which is different from a composition comprising at least one essential oil and from 0.5% to 5% by weight of at least one 4-(3-ethoxy-4-hydroxyphenyl)alkyl ketone compound of formula (I) in which —C—X represents C═O.

3. The composition as claimed in claim 1, which also comprises at least one antiperspirant salt or complex and/or at least one additional deodorant active agent.

4. The composition as claimed in claim 1, wherein the compound of formula (I) is chosen from compounds (1), (2) and (3) below:

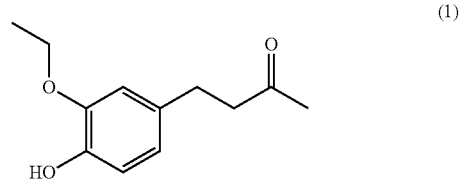

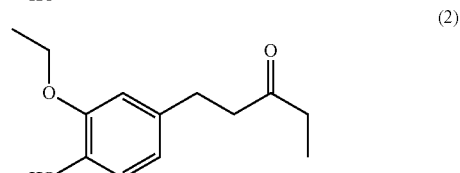

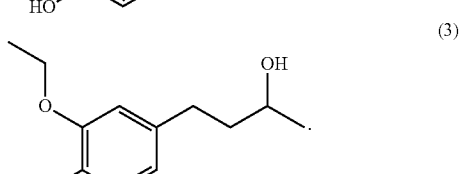

5. The composition as claimed in claim 4, in which the compound of formula (I) is compound (1) of structure:

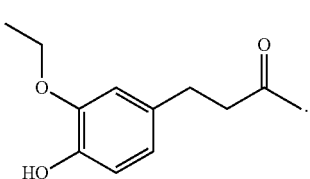

(1)

6. The composition as claimed in claim 1, which comprises 1% to 3% by weight of at least one 4-(3-ethoxy-4-hydroxyphenyl)alkyl ketone compound of formula (I).

7. The composition as claimed in claim 1, which comprises 1% to 3% by weight of the compound of formula (I), wherein the compound of formula (I) is compound (1) of structure:

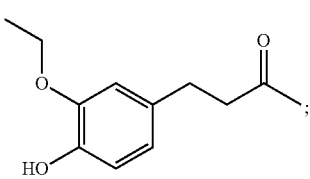

(1)

which also comprises at least one antiperspirant salt or complex and/or at least one additional deodorant active agent and which does not comprise any essential oil.

8. The composition as claimed in claim 1 for treating body odor by reducing the growth of *Corynebacterium xerosis*.

9. A composition, which contains, in a cosmetically acceptable medium, at least one compound of formula (I)

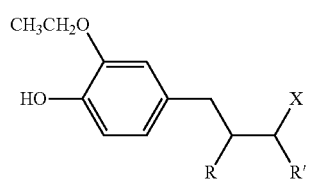

(I)

in which:
- R represents a hydrogen atom, or a linear or branched, saturated or unsaturated (alkyl or alkenyl), $C_1$-$C_6$ hydrocarbon-based radical;
- R' represents a linear or branched, saturated or unsaturated (alkyl or alkenyl), $C_1$-$C_{18}$ hydrocarbon-based radical, optionally substituted with a hydroxyl group;
- C—X represents C=O or CH—OH and at least one antiperspirant salt or complex and/or at least one additional deodorant active agent wherein the composition comprises 1% to 5% by weight of at least one 4-(3-ethoxy-4-hydroxyphenyl)alkyl ketone compound of formula (I) relative to the total weight of the composition and wherein the composition does not comprise an essential oil.

10. The composition as claimed in claim 9, which is different from a composition comprising at least one essential oil and from 0.5% to 5% by weight of at least one 4-(3-ethoxy-4-hydroxyphenyl)alkyl ketone compound of formula (I) in which —C—X represents C=O.

11. The composition as claimed in claim 9, wherein the compound of formula (I) is chosen from compounds (1), (2) and (3) below:

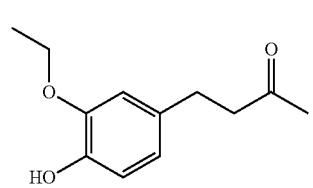

(1)

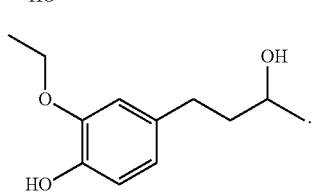

(2)

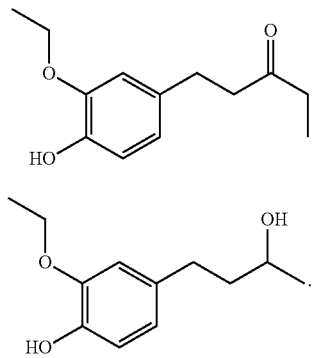

(3)

12. The composition as claimed in claim 11, in which the compound of formula (I) is compound (1) of structure:

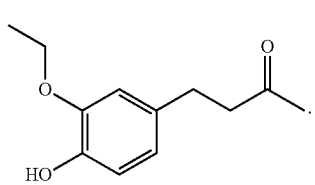

(1)

13. The composition as claimed in claim 9 for treating body odor by reducing the growth of *Corynebacterium xerosis*.

14. A cosmetic process for treating human body odor, which comprises applying to human karatin materials the composition according to claim 1.

15. The process as claimed in claim 14, wherein the compounds of formula (I) are chosen from those for which:
- R represents H, methyl or ethyl,
- R' represents a saturated $C_1$-$C_6$, or unsaturated $C_2$-$C_6$, linear hydrocarbon-based radical, optionally substituted with a hydroxyl group.

16. The process as claimed in claim 14, in which the compounds of formula (I) are chosen from those for which:
- when —C—X represents C=O, R denotes hydrogen and R' represents a linear $C_1$-$C_6$ alkyl radical, optionally substituted with an OH, and more preferentially R' denotes methyl or ethyl; or
- when —C—X represents CH—OH, R denotes hydrogen and R' represents a linear $C_1$-$C_6$ alkyl radical, optionally substituted with an OH, and more preferentially R' denotes methyl or ethyl.

17. The process as claimed in claim 14, wherein the compounds of formula (I) are chosen from compounds (1), (2) and (3) below:

(1)
(2)
(3)
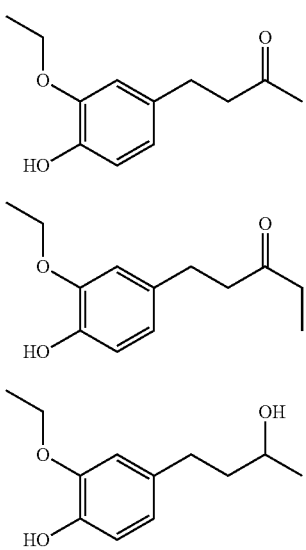
18. The process as claimed in claim 17, in which the compound of formula (I) is compound (1) of structure:
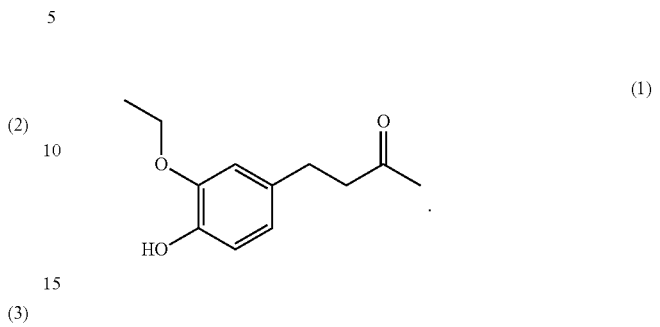
(1)
19. The process as claimed in claim 14, wherein the composition is different from a composition comprising at least one essential oil and from 0.5% to 5% by weight of at least one 4-(3-ethoxy-4-hydroxyphenyl)alkyl ketone compound of formula (I) in which —C—X represents C=O.
* * * * *